United States Patent [19]

Grolman

[11] Patent Number: 5,474,066
[45] Date of Patent: Dec. 12, 1995

[54] NON-CONTACT TONOMETER

[75] Inventor: Bernard Grolman, Worcester, Mass.

[73] Assignee: Leica Inc., Depew, N.Y.

[21] Appl. No.: 188,812

[22] Filed: Jan. 31, 1994

[51] Int. Cl.⁶ ...................................... A61B 3/16
[52] U.S. Cl. ............................................ 128/645
[58] Field of Search .................... 128/630, 645–652, 128/661.06; 351/200, 214, 241

[56] References Cited

U.S. PATENT DOCUMENTS

| | | | |
|---|---|---|---|
| 3,585,849 | 6/1971 | Grolman | 73/80 |
| 3,756,073 | 9/1973 | Lavallee et al. | 73/80 |
| 4,508,121 | 4/1985 | Myers | 128/639 |
| 4,546,773 | 10/1985 | Kremer et al. | 128/661.06 |
| 4,817,620 | 4/1989 | Katsuragi et al. | 128/648 |
| 4,883,061 | 11/1989 | Zeimer | 128/745 |
| 5,042,938 | 8/1991 | Shimozono | 351/205 |
| 5,056,522 | 10/1991 | Matsumura | 128/645 |
| 5,131,739 | 7/1992 | Katsuragi | 128/648 |
| 5,141,302 | 8/1992 | Arai et al. | 351/205 |
| 5,148,807 | 9/1992 | Hsu | 128/648 |

FOREIGN PATENT DOCUMENTS 1560192  4/1990  U.S.S.R. .................... 128/645

Primary Examiner—Angela D. Sykes
Assistant Examiner—Samuel Gilbert
Attorney, Agent, or Firm—Bean, Kauffman & Spencer

[57] ABSTRACT

An improved tonometer is disclosed having a pachymetric device means for measuring a patient's corneal thickness to allow for correction of the intraocular pressure measurement where the corneal thickness measurement deviates from a calibration mean corneal thickness. In a preferred embodiment, a single light source is pulsed just prior to intraocular pressure measurement to illuminate a central corneal section, and a pair of lateral light detector arrays are arranged to obliquely image the corneal section and generate signals which may be processed by a CPU to produce a corneal thickness measurement. If the corneal thickness measurement deviates from the calibration mean corneal thickness, the CPU calculates a thickness-corrected intraocular pressure measurement. The intraocular pressure measurement, corneal thickness measurement, and/or corrected intraocular pressure measurement may then be reported by a suitable display.

32 Claims, 3 Drawing Sheets

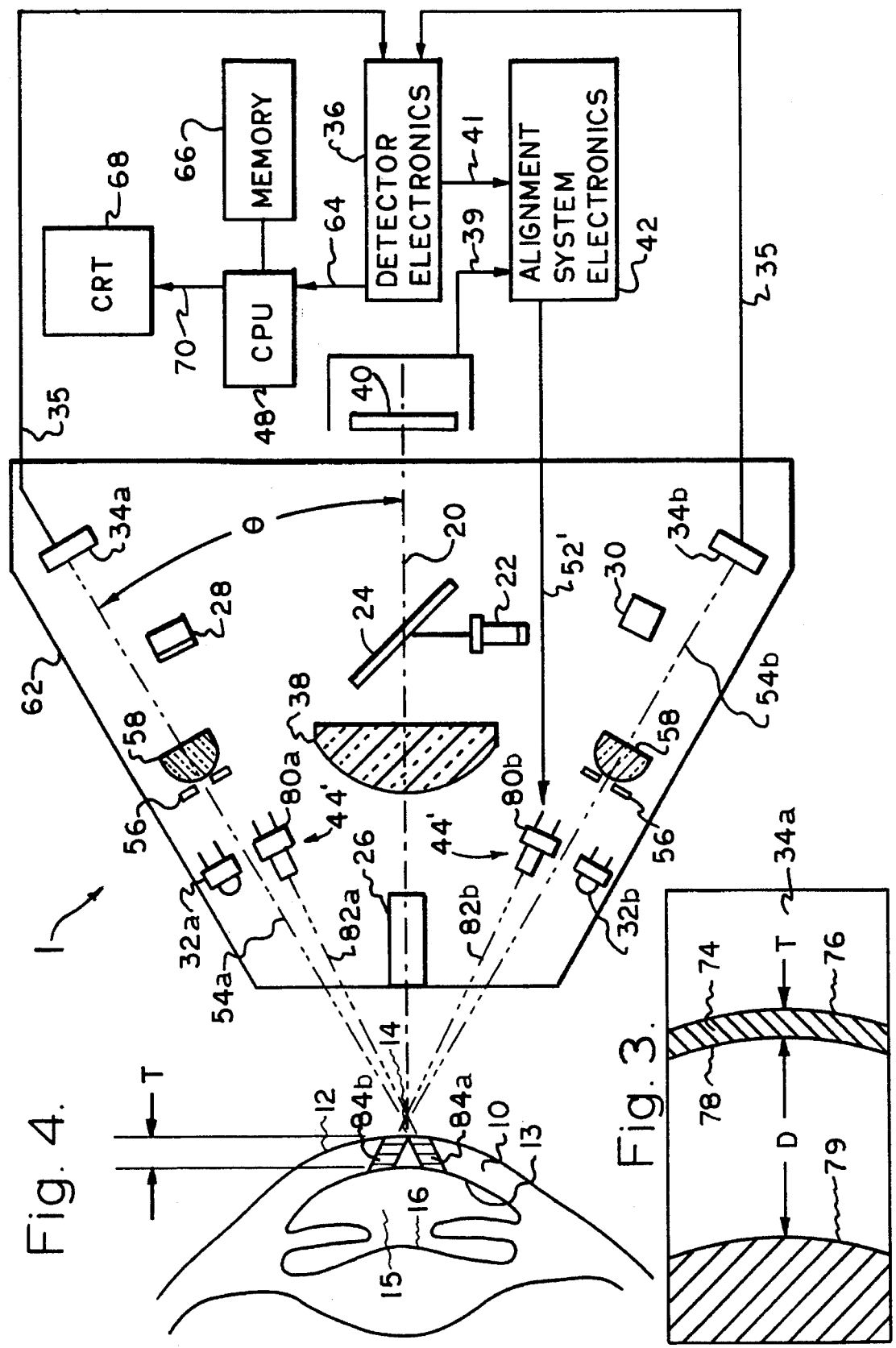

NON-CONTACT TONOMETER

BACKGROUND OF THE INVENTION

It is known to utilize applanation tonometry to measure a patient's intraocular pressure. U.S. Pat. No. 3,585,849, issued on Jun. 22, 1971 to Bernard Grolman, discloses a non-contact tonometer which operates by discharging a fluid pulse of a known force-time relationship onto a cornea of a patient. The resulting deformation of the cornea from convexity through applanation to concavity, and return, is observed as a function of time and correlated to intraocular pressure.

Correlation of the observed deformation with intraocular pressure is carried out using Goldmann's calibration for applanation tonometry, which is based on a calibration mean corneal thickness of 0.52 mm, an approximation of the population mean corneal thickness of 0.522 mm. Since the population standard deviation from the mean population corneal thickness, 0.04 mm, is relatively small, clinical utility of applanation tonometry is preserved for the majority of patients. However, those patients having corneas lying beyond the first standard deviation of thickness are surely candidates for inaccurate intraocular pressure readings. For example, it has been reported in the *American Journal of Ophthalmology*, May 1993, Volume 115, pages 592–596, that for a true intraocular pressure of 20.0 mmHg measured by manometry, a corneal thickness of 0.45 mm produced an intraocular pressure underestimation of 4.7 mmHg by Goldmann applanation tonometry. Consequently, intraocular pressure measurements which do not account for corneal thickness are of compromised reliability as indicators of glaucoma.

SUMMARY OF THE INVENTION

It is therefore an object of the present invention to provide a tonometer with means for measuring a patient's corneal thickness, and means to report such measurement.

Another object is to provide a tonometer with means for calculating and reporting a measurement of the patient's intraocular pressure which has been corrected for corneal thickness deviating from a calibration mean corneal thickness.

Briefly, in accordance with the present invention, a tonometer is provided with pachymetric means for measuring the patient's corneal thickness. More specifically, a non-contact tonometer having a pneumatic system for discharging a fluid pulse onto a patient's cornea, a corneal monitoring system for determining the effect of the fluid pulse on the cornea, and an alignment system for aligning the pneumatic and corneal monitoring systems with a corneal vertex along an alignment axis, is provided with pachymetric means for opto-electronically measuring the corneal thickness of the patient.

Pachymetric means generally includes at least one light source which is pulsed in response to an activation signal, which may be an alignment verification signal from the alignment system, to illuminate a respective sectional region including a cornea section in the vicinity of the corneal vertex, and at least one light detector array for imaging diffusely reflected light from an illuminated sectional region and generating a signal representative of the imaged sectional region. In a preferred embodiment, a single light source is provided on the alignment axis and a pair of light detector arrays are laterally displaced in opposite directions equidistant from the alignment axis to obliquely observe the sectional region illuminated by the light source. In a second embodiment, a pair of light sources are laterally positioned in opposite directions equidistant from the alignment axis and are simultaneously pulsed to illuminate a pair of sectional regions, which are imaged one on each of the lateral light detector arrays.

The detector signals are delivered in digital form to a central processing unit (CPU), which processes the signals to calculate a corneal thickness measurement, given the known geometry of an aligned pachymetric-corneal system. If the corneal thickness measurement deviates from the population mean corneal thickness used to calibrate the tonometer by as much as or more than a predetermined amount, the corneal thickness measurement is preferably used by the CPU to calculate a corrected measurement of the patient's intraocular pressure, which may then be reported by reporting means. Alternatively, the corneal thickness measurement may be reported along with an uncorrected intraocular pressure measurement.

BRIEF DESCRIPTION OF THE DRAWINGS

The nature and mode of operation of the present invention will now be more fully described in the following detailed description taken with the accompanying drawings, in which:

FIG. 3 is a sectional view taken along line 3–3 of FIG. 2 illustrating a sectional region image appearing on a light detector array where the sectional region is illuminated by a vertical line light source; and FIG. 4 is a diagrammatical view of a non-contact tonometer formed in accordance with a second embodiment of the present invention.

DETAILED DESCRIPTION

Figure 1:
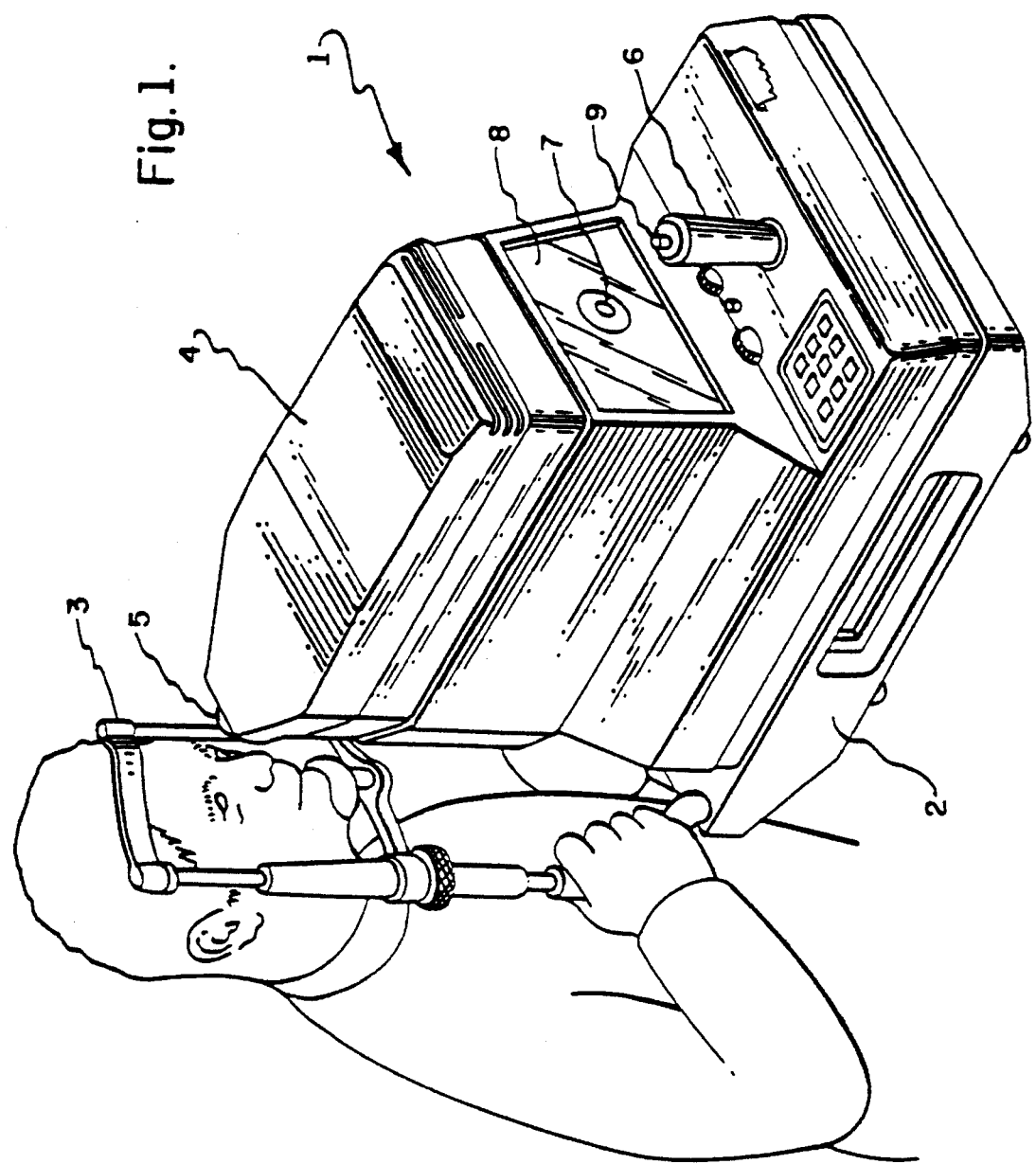
FIG. 1 is a perspective view of a tonometer of a type suitable for use with the present invention.

Referring to FIG. 1, a tonometer is shown generally at 1 and includes a base 2 with a frame 3 to provide a steadying rest for the head of a patient. The test measurement systems (not shown) of tonometer 1 are contained within a housing 4 movably mounted on base 2. Member 5 represents a portion of the instrument to be positioned in a predetermined relationship to the patient's eye. To accomplish this relationship, the operator uses joystick 6 to move housing 4 three dimensionally on base 2, while watching the resulting movement of symbols (not shown) relative to reticle 7 on screen 8. When the operator has achieved alignment by moving housing 4 until the symbols are contained within or superimposed on reticle 7, intraocular pressure measurement is initiated either automatically by tonometer 1, or manually by the operator pressing button 9 on joystick 6. In the alternative, the present invention may be practiced in a tonometer having means for automatically aligning member 5 with the patient's eye.

Figure 2:
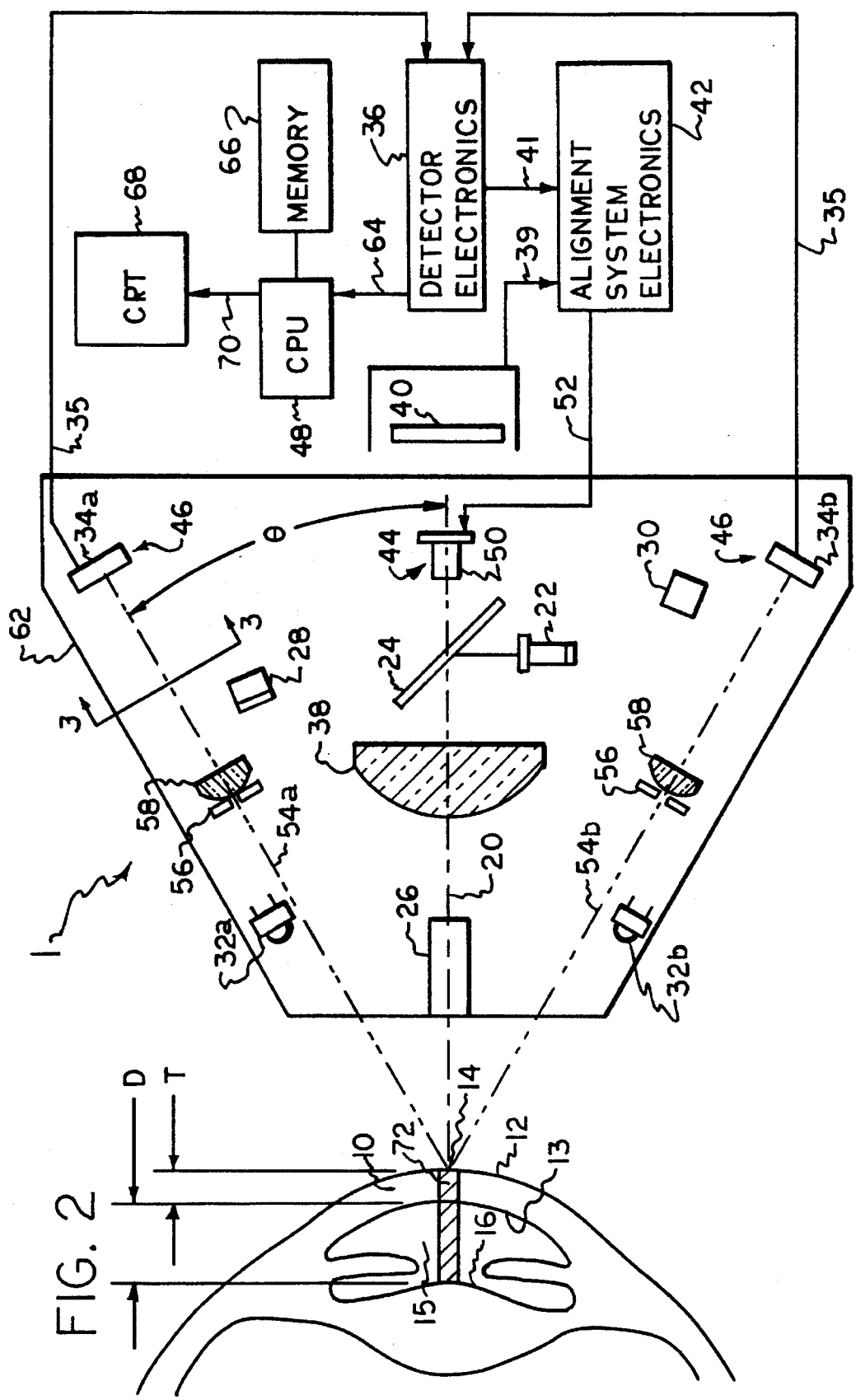
FIG. 2 is a diagrammatical view of a non-contact tonometer formed in accordance with a preferred embodiment of the present invention.

Referring now to FIG. 2, an eye comprises a cornea 10 having a front surface 12, a back surface 13, and a corneal vertex 14, and an anterior chamber 15 extending between back surface 13 and a lens surface 16. Tonometer 1 is schematically represented adjacent cornea 10 and is shown as generally including an alignment axis 20, a fixation source 22 cooperating with a beamsplitter 24 to produce a fixation target centered on the alignment axis, a pneumatic system having an orifice tube 26 for directing a fluid pulse toward cornea 10 along alignment axis 20, a corneal monitoring system generally comprising a light transmitter 28 and corresponding light receiver 30, and an alignment system preferably including a pair of light emitters 32a and 32b, a pair of light detector arrays 34a and 34b connected by leads 35 to detector electronics 36, an objective lens 38, and a video image detector 40 connected to alignment system electronics 42 by lead 39. Detector electronics 36 is connected to alignment system electronics 42 by lead 41. The alignment system permits alignment of corneal vertex 14 with the pneumatic and corneal monitoring systems of tonometer 1 along alignment axis 20, and is preferably of a type disclosed in commonly assigned U.S. Pat. No. 4,881,807 to Luce, et al., however the alignment system may be of a different type comprising different elements without straying from the spirit or scope of the present invention.

Pachymetric means for measuring the thickness T of cornea 10 from front surface 12 to back surface 13 generally comprises illumination means 44 for illuminating at least one sectional region conjugate with or near corneal vertex 14, light detection means 46 for imaging each illuminated sectional region and generating a signal representative of the imaged sectional region, and CPU 48 for processing each signal to calculate a corneal thickness measurement.

In accordance with a preferred embodiment of the present invention, illumination means 44 includes a single light source 50 connected to alignment system electronics 42 by lead 52. Light source 50 preferably produces a collimated beam of light, and may conveniently be a low-powered laser emitting visible light. In the alternative, light source 50 may be an LED which emits light in the infra-red region of the spectrum. Where light source 50 is not a collimated light source, an occluder (not shown) having a small aperture or pin-hole aperture therein may be used in combination with one or more modifying lenses (also not shown) to either collimate light rays from source 50 or cause the light rays to converge at a focal point corresponding to corneal vertex 14. Light source 50 may be of any shape which will provide a sufficiently thin illuminated sectional region, such as a point source, vertical line source, or segmented vertical line source, and is preferably positioned on alignment axis 20 facing cornea 10 such that light emitted thereby is projected toward the cornea. Alternatively, light source 50 may be physically located away from alignment axis 20 and arranged for optical cooperation with suitable projection means, such as beamsplitter 24 or an additional dedicated beamsplitter (not shown) located on the alignment axis, for projecting an image of light source 50 along the alignment axis toward the cornea.

Light detection means 46 includes one or more photosensitive light detector arrays having a plurality of light sensitive areas or pixels thereon, such as a charge-coupled device (CCD), charge-injection device (CID), a vidicon, etc. In the preferred and second embodiments described herein, light detection means 46 includes light detector arrays 34a and 34b, which are also part of the alignment system, however separate light detector arrays may be provided, depending on the type of alignment system and elements therein. Detector arrays 34a and 34b are laterally displaced in opposite directions equidistant from alignment axis 20 and arranged such that their respective axes of observation 54a and 54b intersect at corneal vertex 14, thereby ensuring that the corneal vertex is within the field of observation of each array. An occluder 56 having a small aperture or pin-hole aperture therein and a lens 58 are centered on axes of observation 54a and 54b between the respective detector array and the corneal vertex. Leads 35 connect arrays 34a and 34b to detector electronics 36. Detector arrays 34a and 34b, along with light source 50 and other components of tonometer 1, may be conveniently mounted on a mounting plate 62.

CPU 48 is connected to detector electronics 36 by lead 64, and includes a corresponding memory device 66, such as a RAM. A reporting means 68, such as a cathode-ray tube, liquid crystal display, or the like, is connected to CPU 48 by lead 70.

The mode of operation of the preferred embodiment will now be described with reference to FIGS. 2 and 3. First, cornea 10 is aligned with the pneumatic and corneal monitoring systems of tonometer 1 using the alignment system. Once alignment has been effected, an alignment verification signal is sent by alignment system electronics 42 along lead 52 to light source 50, thereby causing the source to pulse instantaneously, milliseconds prior to intraocular pressure measurement, which is triggered automatically by the alignment system in the preferred embodiment upon satisfaction of predetermined alignment criteria. Where intraocular pressure measurement is not automatically triggered, manual initiation of intraocular pressure measurement by the operator causes an activating signal to be transmitted to light source 50, thereby causing the light source to pulse. A beam of light from light source 50 is projected along alignment axis 20 toward corneal vertex 14. The light incident upon cornea 10 is diffusely scattered as it passes through the corneal medium from front surface 12 to back surface 13, and subsequently through anterior chamber 15 to lens surface 16, thereby illuminating a sectional region which includes a corneal section 72 in the vicinity of corneal vertex 14. Where the invention is practiced with a tonometer having an alignment system which floods the eye with light, such as by light emitters 32a and 32b of the illustrated alignment system, it is desirable to temporarily disable the light emitters of the alignment system immediately prior to illuminating the sectional region with illumination means 44 so that a clear image is produced on detector arrays 34a and 34b.

The illuminated sectional region, and specifically corneal section 72, is obliquely imaged on each of the lateral detector arrays 34a and 34b, thereby defining an associated corneal section image 74 on each array, illustrated in FIG. 3 for detector array 34a where light source 50 is a vertical line source. Each corneal section image 74 is characterized by first and second boundaries, 76 and 78, corresponding to front and back corneal surfaces 12 and 14, respectively. The information gathered by each detector pixel is delivered in analog signal form to detector electronics 36 by leads 35. Detector electronics 36 performs a raster sweep of the analog output signals from each detector array and digitizes the information to produce a series of values representing an X coordinate, a Y coordinate, and the intensity of light received for a given pixel. The digitized image signals are then delivered to CPU 48 by lead 64.

CPU 48 processes the digitized image signals output from detector electronics 36 to calculate a corneal thickness measurement. CPU 48 is programmed to compute the distance T' between first and second boundaries 76 and 78 of image 74 for a pixel row containing the image of corneal vertex 14, based on the number of pixels between boundaries 76 and 78 and the X-axis dimension of each pixel. Given this distance T', and the acute angle $\Theta$ formed by the intersection of the corresponding axis of observation 54a with alignment axis 20, which may be stored as a system parameter, the corneal thickness T may be calculated trigonometrically by CPU 48. In the preferred embodiment, corneal thickness T is proportional to distance T' divided by sine Θ. Since both detector arrays 34a and 34b detect light from the same corneal section 72 in the preferred embodiment, processing signals originating therefrom theoretically provides a pair of redundant values indicative of a central corneal thickness, however such values are likely to differ slightly due to imperfect symmetry of cornea 10 and detector arrays 34a and 34b about alignment axis 20. One of the corneal thickness values may be chosen, or the values may be averaged by CPU 48, to generate a corneal thickness measurement for storage by memory device 66.

Pachymetric means is preferably capable of measuring the depth D of anterior chamber 15, that being the distance from back surface 13 to lens surface 16, in addition to corneal thickness T. Such capability is diagnostically useful, since patients having a shallow anterior chamber are more vulnerable to narrow angle acute glaucoma. Measurement of anterior chamber depth is performed in substantially the same manner as measurement of corneal thickness, with lens surface 16 providing a change in light scattering medium which may be imaged by detector arrays 34a and 34b. In FIG. 3, the image of lens surface 16 appears as a third boundary 79 on detector array 34a, with the distance D' from second boundary 78 to third boundary 79 being proportional to the anterior chamber depth.

Immediately after light source 50 has been pulsed for purposes of measuring corneal thickness, the pneumatic and corneal monitoring systems of the tonometer are triggered and cooperate in a known manner to produce an intraocular pressure measurement which may be stored by memory device 66. CPU 48 is preferably programmed to compare the corneal thickness measurement with a mean population corneal thickness value used to calibrate tonometer 1 and stored by memory device 66, and calculate a thickness-corrected intraocular pressure measurement where the corneal thickness measurement deviates from the calibration corneal thickness by as much as or more than a predetermined amount.

Correction of the intraocular pressure measurement may be carried out by fitting the corneal thickness measurement to an empirically generated regression equation which correlates corneal thickness to the amount of measurement error from true intraocular pressure, and then correcting the intraocular pressure measurement to account for the measurement error. Table 1 lists approximate measurement error from true intraocular pressure associated with selected corneal thicknesses, assuming a linear relationship, and the corresponding correction to be added to the intraocular pressure measurement. Table 1 is provided for purposes of illustration only, and use of a more comprehensive set of data points and/or a non-linear regression equation is contemplated.

TABLE 1

| CORNEAL THICKNESS (mm) | ERROR (mmHg) | CORRECTION (mmHg) |
|---|---|---|
| 0.38 | −9.1 | 9.1 |
| 0.45 | −4.6 | 4.6 |
| 0.50 | −2.7 | 2.7 |
| 0.522 | 0.0 | 0.0 |
| 0.56 | 2.4 | −2.4 |
| 0.62 | 6.2 | −6.2 |
| 0.72 | 12.6 | −12.6 |

The thickness-corrected intraocular pressure measurement calculated by CPU 48 may then be reported to a practitioner by reporting means 64. The corneal thickness measurement and/or uncorrected intraocular pressure measurement may also be reported in addition to, or in lieu of, the corrected intraocular pressure measurement.

Referring now to FIG. 4, a second embodiment of the present invention is shown schematically. The second embodiment operates in substantially the same manner as the preferred embodiment, however pachymetric means in the second embodiment is of an alternative construction. Specifically, illumination means 44' in the second embodiment comprises a pair of light sources 80a and 80b laterally displaced in opposite directions equidistant from alignment axis 20. Both light sources 80a and 80b are caused to pulse simultaneously immediately subsequent to alignment of cornea 10 along alignment axis 20, preferably by an alignment verification signal transmitted from alignment system electronics 42 through lead 52'. Light from sources 80a and 80b is directed along corresponding sectional axes 82a and 82b toward corneal vertex 14 to illuminate a pair of lateral corneal sections 84a and 84b, respectively. Diffusely reflected light from corneal section 84a is obliquely imaged on detector array 34b, while light from corneal section 84b is likewise obliquely imaged on opposite detector array 34a.

Detector signals representing illuminated corneal sections 84a and 84b are digitized by detector electronics 36 and delivered CPU 48, where they are processed in a manner similar to that described above with regard to the preferred embodiment. Given that both axes of observation 54a and 54b of the detector arrays intersect alignment axis 20 at aligned corneal vertex 14 to form a known angle relative to alignment axis 20, corneal thickness in the vicinity of corneal sections 84a and 84b may be computed trigonometrically by CPU 48 from the detector signals. The pair of corneal thickness values so obtained may then be averaged by CPU 48 to yield a single corneal thickness measurement, which may be stored by memory device 66 and utilized as described above with regard to the preferred embodiment.

What is claimed is:

1. An ophthalmic instrument comprising a housing and testing means for testing an eye of a patient mounted within said housing, said testing means having an alignment axis alignable with a corneal vertex of said eye of said patient, tonometric means for measuring intraocular pressure of said eye without contacting said eye, and pachymetric means for measuring corneal thickness of said eye without contacting said eye.

2. The instrument according to claim 1, wherein said pachymetric means opto-electronically measures said corneal thickness.

3. The instrument according to claim 2, wherein said pachymetric means comprises:

illumination means for illuminating at least one sectional region of an eye, said sectional region including a corneal section;

light detection means for imaging light from said sectional region and generating a signal representative of said sectional region; and CPU means for processing said signal to compute said corneal thickness measurement.

4. The instrument according to claim 3, wherein said sectional region includes an anterior chamber section of said eye and said CPU means processes said signal to compute an anterior chamber depth measurement.

5. The instrument according to claim 3, wherein said illumination means includes at least one light source and projection means to project an image of said light source toward said cornea along a sectional axis intersecting said cornea in a vicinity of said corneal vertex to illuminate said sectional region.

6. The instrument according to claim 5, wherein said illumination means includes a plurality of light sources for illuminating a plurality of sectional regions.

7. The instrument according to claim 5, wherein said light source includes a point source.

8. The instrument according to claim 5, wherein said light source includes an occluder having a small aperture or pin-hole aperture therein.

9. The instrument according to claim 5, wherein said light source includes a collimated light source.

10. The instrument according to claim 9, wherein said light source includes a laser.

11. The instrument according to claim 5, wherein said light source includes an infra-red source.

12. The instrument according to claim 5, wherein said light source includes a vertical line source.

13. The instrument according to claim 3, wherein said light detection means includes at least one charge-coupled device.

14. The instrument according to claim 3, further comprising reporting means for reporting said intraocular pressure measurement and said corneal thickness measurement.

15. The instrument according to claim 14, wherein said reporting means includes a visual display.

16. The instrument according to claim 3, wherein said CPU means calculates a corrected intraocular pressure measurement using said corneal thickness measurement.

17. The instrument according to claim 16, further comprising reporting means for reporting said intraocular pressure measurement, said corneal thickness measurement, and said corrected intraocular pressure measurement.

18. The instrument according to claim 17, wherein said reporting means includes a visual display.

19. In a non-contact tonometer of a type having an alignment axis, a fixation target centered on said alignment axis, a pneumatic system in which a fluid pulse is directed toward a cornea of a patient, a corneal monitoring system in which the effect of said fluid pulse on said cornea is determined, an alignment system for aligning said pneumatic and monitoring systems relative to said cornea, and control means for controlling said pneumatic, monitoring and alignment systems to generate an intraocular pressure measurement, the improvement comprising: pachymetric means alignable relative to said cornea by said alignment system for measuring thickness of said cornea without contacting said cornea in response to an activation signal.

20. The improvement according to claim 19, wherein said activation signal is an alignment verification signal sent by said alignment system when a vertex of said cornea has been aligned relative to said pneumatic and monitoring systems along said alignment axis.

21. The improvement according to claim 20, wherein said pachymetric means comprises illumination means connected to said alignment system for illuminating at least one corneal section in response to said alignment verification signal; at least one light detector array for imaging said corneal section and generating a signal representative of said corneal section, each said array having a field of observation inclusive of said corneal vertex; and CPU means for processing said signal to calculate said corneal thickness measurement.

22. The improvement according to claim 21, wherein said illumination means includes a light source and projection means for projecting an image of said light source along said alignment axis toward said cornea.

23. The improvement according to claim 22, wherein said light source is located on said alignment axis.

24. The improvement according to claim 22, wherein said light source is displaced from said alignment axis.

25. The improvement according to claim 24, wherein said projection means includes a beamsplitter arranged to receive an image of said light source and project said image toward said cornea along said alignment axis.

26. The improvement according to claim 21, wherein said illumination means includes a plurality of light sources and projection means for projecting an image of each said light source toward said cornea along a sectional axis intersecting said cornea in a vicinity of said corneal vertex to illuminate said corneal section.

27. The improvement according to claim 26, wherein said plurality of light sources includes a pair of light sources laterally displaced in opposite directions equidistant from said alignment axis.

28. The improvements according to claim 21, wherein two said arrays are laterally displaced in opposite directions equidistant from said alignment axis, each said array having a field of observation inclusive of said corneal vertex.

29. The improvement according to claim 27, wherein two said arrays are laterally displaced in opposite directions equidistant from said alignment axis, each said array having a field of observation inclusive of said corneal vertex.

30. The improvement according to claim 21, further comprising reporting means for reporting said corneal thickness measurement.

31. The improvement according to claim 21, wherein said CPU means calculates a corrected intraocular pressure measurement using said corneal thickness measurement.

32. The improvement according to claim 31, further comprising reporting means for reporting said intraocular pressure measurement, said corneal thickness measurement, and said corrected intraocular pressure measurement.

* * * * *